United States Patent
Alexandrescu

(10) Patent No.: US 6,272,368 B1
(45) Date of Patent: Aug. 7, 2001

(54) MEDICAL INSTALLATION HAVING AN APPARATUS FOR ACQUIRING THE POSITION OF AT LEAST ONE OBJECT LOCATED IN A ROOM

(75) Inventor: Mircea Alexandrescu, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/164,312

(22) Filed: Oct. 1, 1998

(30) Foreign Application Priority Data

Oct. 1, 1997 (DE) .............................. 197 43 500

(51) Int. Cl.[7] ...................................................... A61B 5/05
(52) U.S. Cl. .................... 600/407; 600/473; 600/476; 600/477; 250/358.1; 250/574; 250/349; 345/158
(58) Field of Search .................................. 600/312, 473, 600/476, 477, 407; 250/358.1, 574, 349; 128/897, 653.1; 364/559, 516; 345/158

(56) References Cited

U.S. PATENT DOCUMENTS

| 5,486,700 | 1/1996 | Silberklang et al. . |
| 5,622,187 | * 4/1997 | Carol .................................... 128/897 |
| 5,630,431 | * 5/1997 | Taylor ................................... 128/897 |
| 5,729,475 | * 3/1998 | Romanik, Jr. ........................ 702/150 |

FOREIGN PATENT DOCUMENTS

OS 36 04 955   8/1987 (DE) .
PS 43 35 301  12/1994 (DE) .

* cited by examiner

Primary Examiner—Marvin M. Lateef
Assistant Examiner—Jeoyuh Lin
(74) Attorney, Agent, or Firm—Schiff Hardin & Waite

(57) ABSTRACT

A medical installation, having an apparatus for acquiring the position of at least one object located in a room, also has a light transmitter for emitting a light fan and a camera for acquiring at least one object. The signals of the camera are supplied to an evaluation unit that generates 3D data on the basis of these signals corresponding to the at least one object that are utilized for avoiding collisions of the object.

12 Claims, 5 Drawing Sheets

FIG 1

MEDICAL INSTALLATION HAVING AN APPARATUS FOR ACQUIRING THE POSITION OF AT LEAST ONE OBJECT LOCATED IN A ROOM

BACKGROUND OF THE INVENTION

1. Field of the Invention

The present invention is directed to a medical installation of the type having a number of components which are adjustable in position within an examination room, and during such adjustment are subject to possible collisions with each other and/or with persons in the examination room.

2. Description of the Prior Art

In medical installations, for example an x-ray diagnostics installation with adjustable components, the image generating system can have a C-shaped arc as a component that is adjustable along its circumference at a holder, this arc carrying an x-ray radiator and a radiation receiver at its ends. The image generating system can thus be optimally adjusted for the transirradiation of an examination subject from different directions. To this end, for example, the table for the examination subject can also be adjustable in height and in a plane as a further component.

Given an x-ray diagnostics installation of this type, there is the risk that the adjustable components will come too close to the examination subject, even touch the examination subject under certain substances and thereby jeopardize his or her safety. In order to avoid such a risk, limit switches can be provided at the adjustable components that effect a standstill of, for example, the adjustment motor of the component when such components strike an obstacle.

In order to avoid this risk, German OS 36 04 955 already discloses that the adjustable components be provided with sensors that report the respective position of the components to a computer. The computer compares this position to an envelope erected over the bearing device and signals when one of the adjustable components touches the envelope. It is thereby possible to avoid a collision.

In a medical system disclosed by German OS 43 35 301, a collision is avoided without complicated mathematical model formation but still taking moveable obstacles into consideration, for example by using the patient monitoring. To this end, video cameras are provided for monitoring the room of the medical system, whereby an electronics combines the coordinates of the contours of the components and of the obstacles to form a multi-dimensional vector and forwards this to a three-dimensional neural network that blocks movements that would lead to collisions.

SUMMARY OF THE INVENTION

An object of the present invention is to provide a medical installation of the type initially described wherein, in particular, collisions of components of the medical devices with one another as well as collisions with unknown objects freely moveable in space, for example with persons, can be avoided and that the outlay required therefor is low in view of the structural implementation.

This object is achieved in accordance with the invention in a medical installation having an apparatus for acquiring the position of at least one object located in a room, including a light transmitter for emitting a narrow light fan as well as a camera for acquiring the at least one object. The signals of the camera are supplied to an evaluation unit that generates 3D data corresponding to the at least one object on the basis of these signals, the 3D data being used in order to avoid collisions of the object. Sensors at the components can thus be foregone and the medical installation is compact and simple in structure.

It is especially advantageous when the evaluation unit evaluates the signals of the camera in view of the active or passive triangular 3D technique, as a result of which data are obtained corresponding to the spatial arrangement of the at least one object.

It is also advantageous when the light transmitter generates a two-dimensional light fan with which, in particular, the room in which the medical installation is arranged can be optically scanned. The scanning of the room is thus especially good and a large amount of data can be received from the camera within a short time.

It is particularly advantageous for the light transmitter to be an infrared light source since infrared light cannot be perceived by an operator or by the examination subject, so that it is not disturbing.

Environmental influences due to the ambient light can be excluded in the signal generation by placing an infrared filter in front of the camera, preferably a narrow-band infrared filter.

DESCRIPTION OF THE PREFERRED EMBODIMENTS

Figure 1:
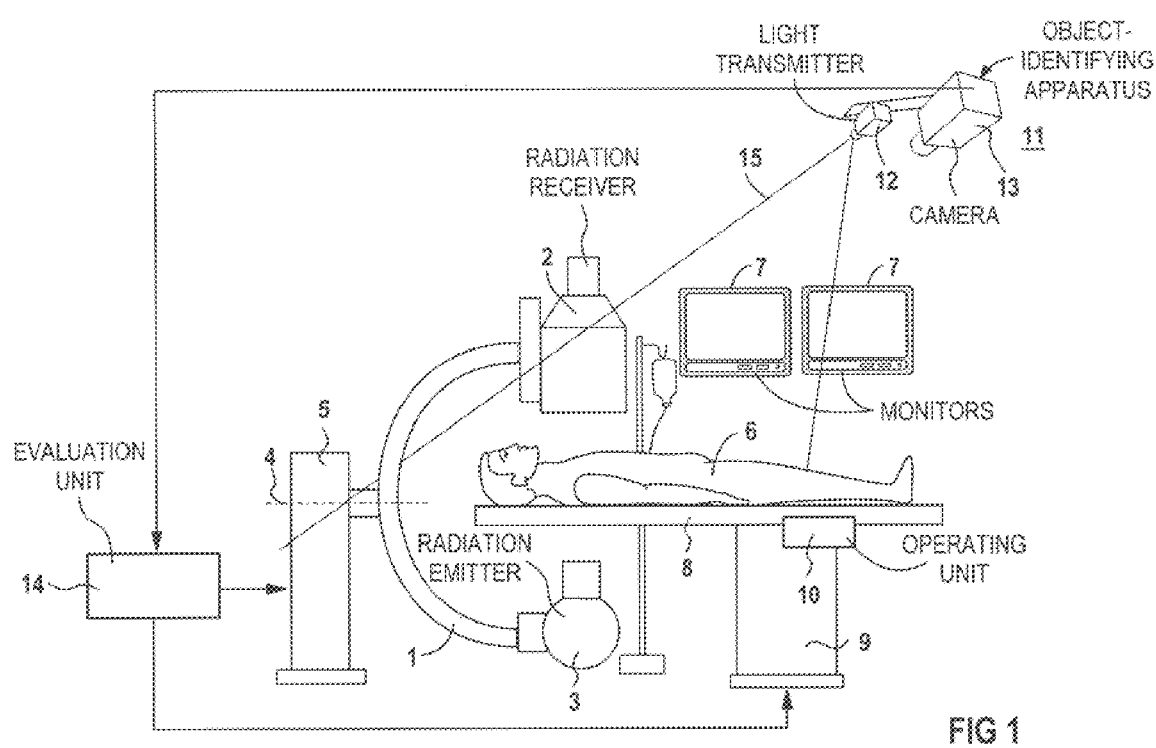
FIG. 1 shows an exemplary embodiment of a medical installation of the invention with an apparatus for acquiring an object.

The medical installation shown as exemplary embodiment in FIG. 1 is as an x-ray diagnostic device that has a C-arm 1 at whose ends a radiation receiver 2 and a radiation emitter 3 are arranged lying opposite one another. The C-arm 1 is preferably adjustable along its circumference as well as around a horizontal axis 4 at a column 5, so that an examination subject 6 can be transirradiated from different directions. The signals of the radiation receiver 2 are supplied to an evaluation and control unit (not shown), so that an image of the examined region of the examination subject 6 can be displayed on a monitor 7 on the basis of these signals in a known way. As shown in FIG. 1 the examination subject 6 is arranged on a plate 8 that is adjustable at a base 9, for example in height and/or along its longitudinal and transverse axes, and may also be mounted so as to be swivelable. Via an operating unit 10 arranged at the base 9, the physician or the operator of the medical installation, for example, can control and adjust the components.

Figure 5:
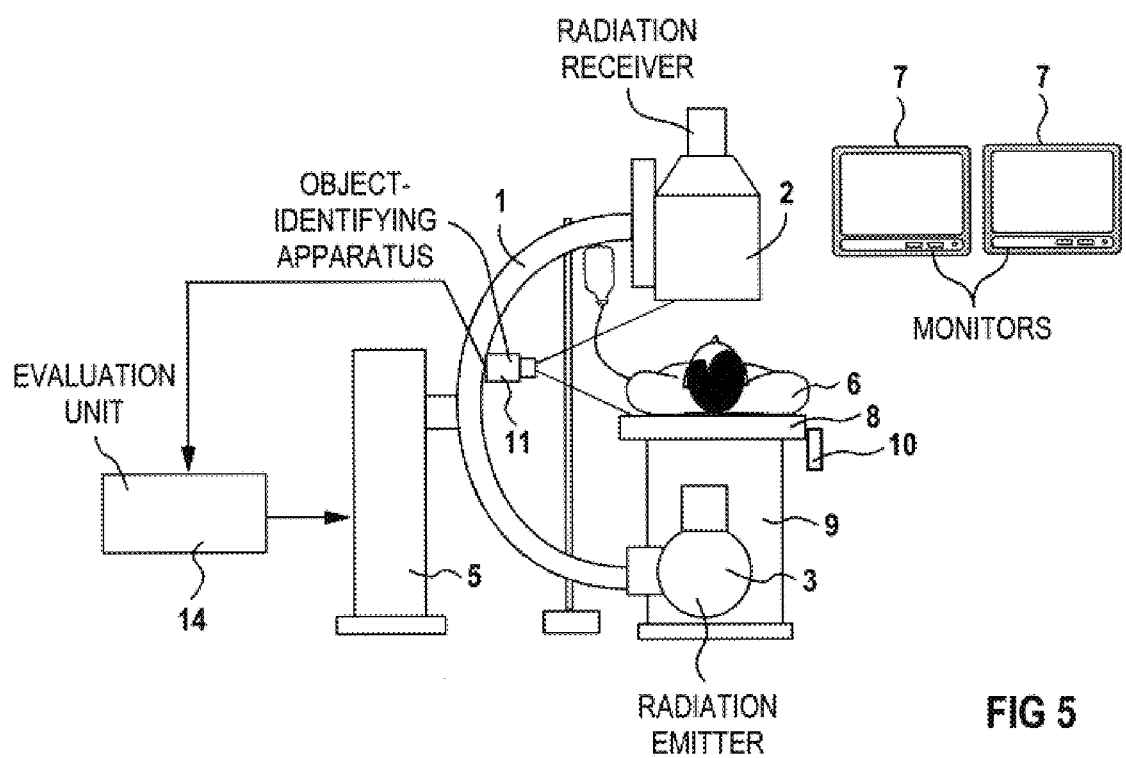
FIG. 5 shows an apparatus arranged at a device part in accordance with the invention.

In order to avoid adjustment of the positions of the components of the medical installation, for example the radiation receiver 2, the radiation emitter 3 and/or the plate 8 and/or control systems, etc., causing a collision with one another and/or with the examination subject 6, the operator or the monitors 7 or with other parts or objects located in the room, referred to in general below as objects, an apparatus 11 for acquiring the position of at least one object located in the room of the medical installation is inventively provided. As can be seen from FIG. 2 the apparatus 11 includes a light transmitter 12 and a camera 13 as well as an evaluation unit 14 following the camera 13 that influences the control unit of the medical installation. As can be seen from FIG. 1 the apparatus 11 is arranged at the ceiling of a room. Within the framework of the invention, further apparatuses 11 for monitoring the room can be provided; it is also possible to arrange the apparatus 11 at, for example, a side wall of the room and/or at an apparatus part in conformity with the exemplary embodiment according to FIG. 5, for example at the C-arm 1. The only mounting criterion is that at least the range of adjustment of the components of the medical installation must be covered and scanned with the light fan 15 emanating from the light transmitter 12 and must be received with the camera 13.

Figure 2:
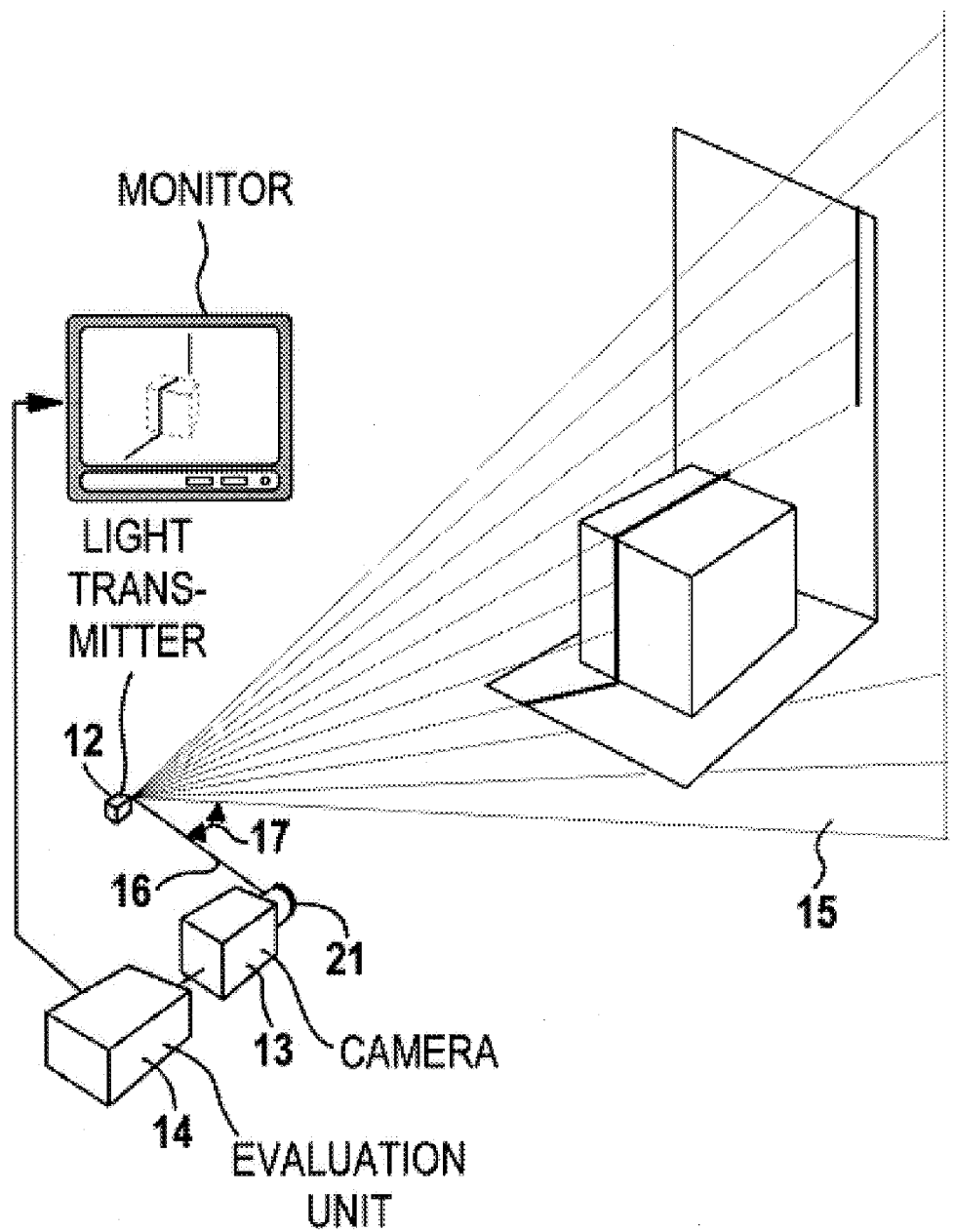
FIG. 2 shows the apparatus of FIG. 1 in more detail.

FIG. 2 shows the apparatus 11 in more detail, wherein elements already explained in FIG. 1 are identified with the same reference characters. One of the possibilities of covering all of the aforementioned objects and their arrangement in the room is the utilization of the active triangular 3D technique known from the literature. Given a two-dimensional illumination emanating from the light transmitter 12, for example with a light curtain or with a light fan 15, and given a two-dimensional scanning of the room with the camera 13 that, for example, can be implemented as a video camera as video/CCD camera, highly exact 3D data with respect to the positions of the objects in the room can be acquired given a known optical base 16 between the light transmitter 12 and the camera 13 and given a known illumination angle 17. As already explained, these 3D data are utilized for "supervising" the adjustment control, particularly in view of avoiding collisions of the components of the medical installation.

Figure 3:
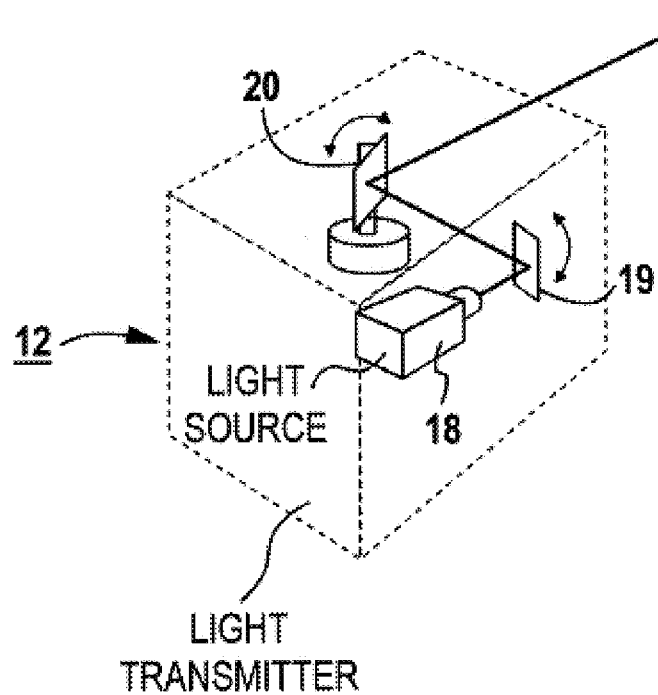
FIG. 3 shows an exemplary embodiment of a light transmitter of the apparatus of FIG. 2.

As proceeds from FIG. 3, a light source 18 can transmit a narrow light beam for generating a two-dimensional light fan 15, this light beam being deflected via a first mirror 19 or a cylinder lens in a first plane, for example in a vertical direction, and being deflected via a second mirror 20 in a second plane aligned approximately perpendicularly relative to the first direction, for example in the horizontal direction. A light fan 15 for scanning at least a sub-region of the room can thus be generated. The adjustment of the first mirror 19 is preferably synchronized with the generation of signals of a first frame of the camera 13 so that each frame is based, for example, on a scan in the first plane, for example the vertical plane. The signals of the camera 13 are then supplied to the evaluation unit 14 that includes a calculating unit as well as a memory in which the data calculated by the calculating unit are stored corresponding to the momentary arrangement of the objects, and are thus made accessible for further processing. For example, the surfaces of the radiation receiver 2 can be compared to the surfaces of the examination subject 6 in view of the spacing and a control signal can be generated when the radiation receiver 2 and the examination subject 6 approach one another in an impermissible manner. Further adjustment of the radiation receiver 2 and of the examination subject 6 in a direction toward one another is then precluded on the basis of the signal.

Figure 4:
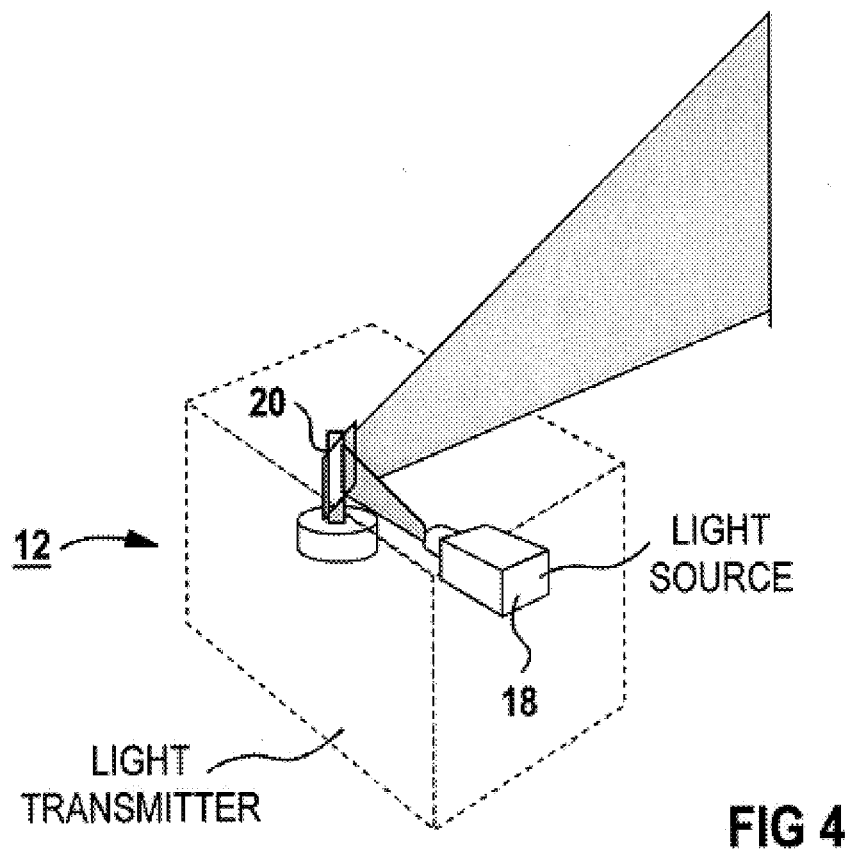
FIG. 4 shows a further exemplary embodiment of a light transmitter of the apparatus of FIG. 2.

Within the scope of the invention, the light source 18 according to FIG. 4 can also emit a light fan in a first plane generated with, for example, a cylinder lens or a mask, this being deflected via a mirror 20 in a second plane.

Preferably, the light transmitter 18 is an infrared light transmitter that, for example, is an infrared laser or an infrared emitting semiconductor component. The infrared light cannot be perceived by the operator or by the examination subject 6 and is therefore not disturbing in the examination. A narrow-band infrared filter 21 that allows only the light of the infrared light source 18 to pass can be provided in front of the camera 13, so that reflections and unwanted influences emanating from the ambient light can be excluded to a maximum extent in the generation of the signals by the camera 13.

Figure 6:
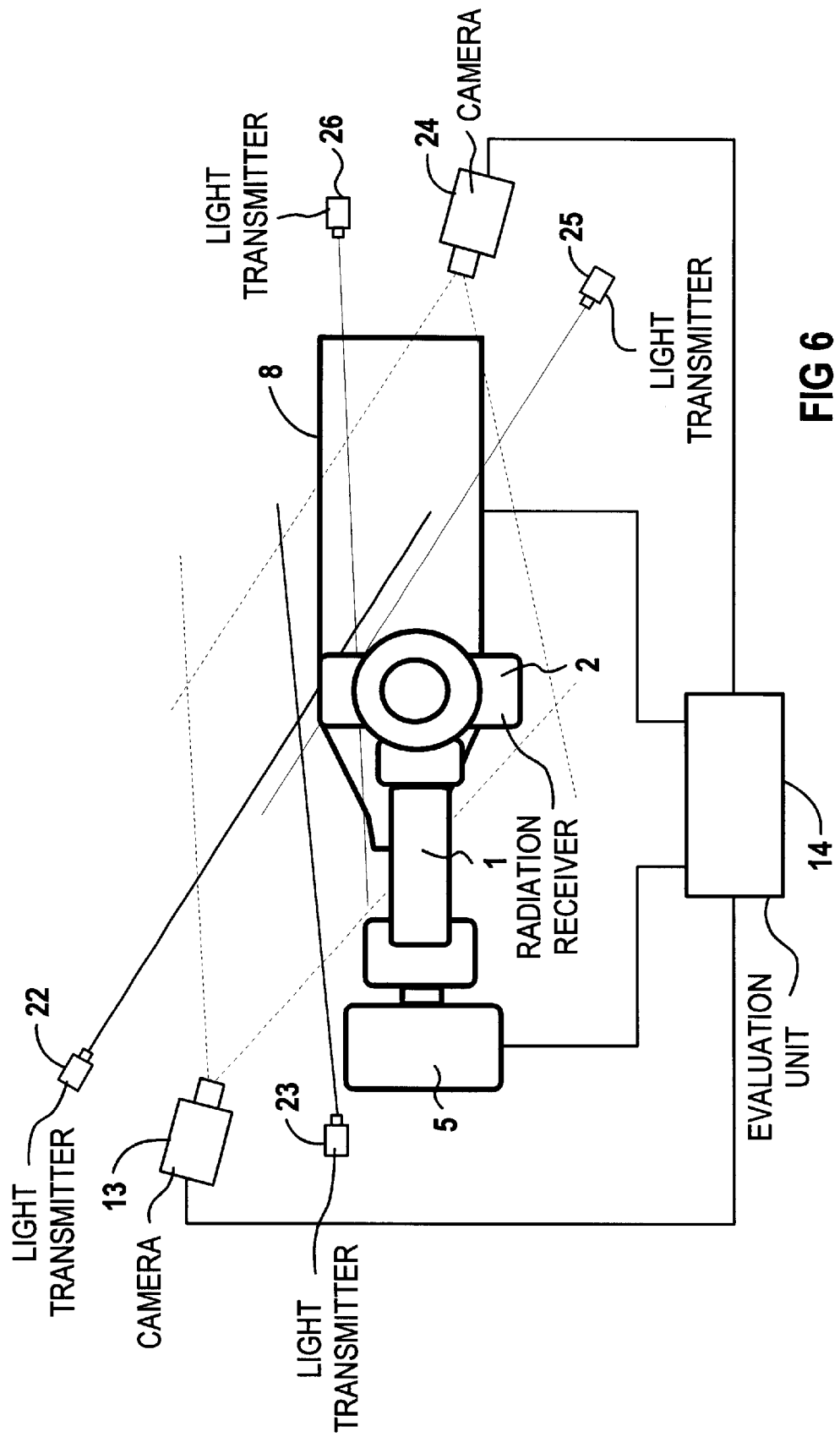
FIG. 6 shows a medical installation according to FIG. 1 with a number of apparatuses for acquiring an object.

As already explained, it has proven advantageous to arrange an apparatus 11 at the ceiling of the room since it is thus not disturbing and a good "overview" is assured. In order to avoid any occlusions which may occur in the scanning of the objects with the light fan 15, a bilateral illumination can also ensue, for which, for example, a second apparatus is provided in conformity with FIG. 6 that scans the room from another direction. The calculating unit thereby correlates the respectively received signals of the cameras 13, 24, so that a complete 3D image, but at least data from all objects in the room, can be generated.

To this end, a first and second light transmitters 22, 23 can be allocated to a first camera 13. First image signals are derived from the camera 13 and supplied to the evaluation unit 14 upon activation of the first light transmitter 22. The first light transmitter 22 is then shut off and the second light transmitter 23 is turned on and two image signals proceeding from the camera 13 are likewise supplied to the evaluation unit 14. The evaluation unit 14 operates on the first and second image signals to form image signals corresponding to a perspective or three-dimensional presentation of the objects. Control signals are then generated from these image signals dependent on the distance of the objects from one another. For further completion and observation of the room or of the distance of the objects from one another, a further camera 24, as proceeds from FIG. 6, having a further, allocated first and/or second light transmitters 25, 26 can be provided with which the room or the objects can be "observed" from a different prospective. The further first and second light transmitters 25, 26 can also be driven in alternation to generate further first and second image signals, and the further first and second image signals obtained from the further camera 24 can be supplied to the evaluation unit 14 for generating control signals. A further improvement is thus achieved in the monitoring and the prevention of a collision.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical installation for use in an examination room, comprising:

a plurality of moveable installation components in an examination room, each of said components having a movement controller which controls movement of that component in said examination room;

a light transmitter which emits a light fan within a field of view including at least one of said components;

a camera disposed remote from said components for acquiring an image, including said at least one component, irradiated by said light fan and producing camera signals corresponding to said image; and evaluation means, connected to each said movement controller, supplied with said camera signals for generating three-dimensional data from said camera signals identifying a position of said at least one component in said examination room and for controlling the movement controller of said at least one component for preventing collision of said at least one component with other installation components and with persons in said examination room.

2. A medical installation as claimed in claim 1 wherein said light transmitter comprises means for emitting a two-dimensional light fan.

3. A medical installation as claimed in claim 2 wherein said light transmitter comprises means for emitting a light beam and includes a first mirror on which said light beam is incident for deflecting said light beam in a first plane to produce a deflected beam, and a second mirror in which said deflected beam is incident for deflecting said deflected beam in a second plane to produce said light fan, said second plane being oriented substantially perpendicularly to said first plane.

4. A medical installation as claimed in claim 3 wherein said camera generates said camera signals in a plurality of frames including a first frame followed by successive frames, and further comprising means for moving said first mirror to conduct a plurality of successive scans of said examination room in said first plane including a first scan followed by a plurality of successive scans, and for synchronizing said first scan with said first frame and each of said successive scans respectively with said successive frames.

5. A medical installation as claimed in claim 1 wherein said light transmitter comprises means for emitting a fan-shaped light beam as said light fan, said fan-shaped light beam being disposed in a first plane, and wherein said light transmitter further comprises a mirror for moving said fan-shaped light beam in a second plane for scanning said examination room in successive scans in said second plane, said second plane being oriented substantially perpendicularly to said first plane, and wherein said camera signal comprises a plurality of successive frames, and means for synchronizing movement of said mirror for synchronizing said scans in said second plane with said frames in said camera signal.

6. A medical installation as claimed in claim 1 wherein said light transmitter comprises an infrared light source.

7. A medical installation as claimed in claim 6 further comprising an infrared filter disposed in front of said camera allowing only light from said infrared light source to pass through said infrared filter.

8. A medical installation as claimed in claim 6 wherein said infrared light source comprises an infrared laser.

9. A medical installation as claimed in claim 1 wherein said camera comprises a CCD camera.

10. A medical installation as claimed in claim 1 wherein said light transmitter is disposed at a ceiling of said examination room.

11. A medical installation as claimed in claim 1 further comprising at least one means for producing an additional set of three-dimensional data of said at least one object in said examination room, and means for correlating said three-dimensional image with said at least one further set of three-dimensional data for avoiding said collisions.

12. A medical installation as claimed in claim 1 wherein said camera comprises a television camera.

* * * * *